US008753379B1

(12) United States Patent
Frei et al.

(10) Patent No.: US 8,753,379 B1
(45) Date of Patent: Jun. 17, 2014

(54) SURGICAL GUIDE BODY

(75) Inventors: Reto Frei, Davos Platz (CH); Markus Hehli, Davos Frauenkirch (CH); Georg Duda, Berlin (DE)

(73) Assignee: Depuy Synthes Products, LLC, Raynham, MA (US)

(*) Notice: Subject to any disclaimer, the term of this patent is extended or adjusted under 35 U.S.C. 154(b) by 3925 days.

(21) Appl. No.: 10/240,526

(22) PCT Filed: Mar. 7, 2000

(86) PCT No.: PCT/CH00/00129

§ 371 (c)(1), (2), (4) Date: Sep. 30, 2002

(87) PCT Pub. No.: WO01/12081

PCT Pub. Date: Feb. 22, 2001

(30) Foreign Application Priority Data

Aug. 11, 1999 (DE) .............................. 299 13 944 U

(51) Int. Cl.
*A61B 17/80* (2006.01)

(52) U.S. Cl.
CPC ......... *A61B 17/8047* (2013.01); *A61B 17/8057* (2013.01); *A61B 17/8085* (2013.01)
USPC ........................................... 606/288; 606/285

(58) Field of Classification Search
CPC .................................................. A61B 17/8047
USPC ........... 606/69–71, 96, 61, 286, 288; 411/178
See application file for complete search history.

(56) References Cited

U.S. PATENT DOCUMENTS

| | | | | |
|---|---|---|---|---|
| 3,741,205 A | | 6/1973 | Markolf et al. | 128/92 B |
| 3,867,932 A | * | 2/1975 | Huene | 606/80 |
| 4,484,570 A | * | 11/1984 | Sutter et al. | 606/282 |
| 5,375,956 A | * | 12/1994 | Pennig | 411/389 |
| 5,474,553 A | * | 12/1995 | Baumgart | 606/71 |
| 5,476,467 A | | 12/1995 | Benoist | 606/100 |
| 5,527,311 A | * | 6/1996 | Procter et al. | 606/280 |
| 5,607,428 A | * | 3/1997 | Lin | 606/287 |
| 5,643,264 A | * | 7/1997 | Sherman et al. | 606/61 |

(Continued)

FOREIGN PATENT DOCUMENTS

| | | |
|---|---|---|
| EP | 0 558 789 A1 | 9/1993 |
| EP | 0 705 572 A2 | 4/1996 |

(Continued)

OTHER PUBLICATIONS

U.S. Appl. No. 60/044,190. Ray, Charles D. Apr. 25, 1997.*

*Primary Examiner* — David H Willse
(74) *Attorney, Agent, or Firm* — Fay Kaplun & Marcin, LLP

(57) ABSTRACT

A guide body is designed to receive longitudinal fixation elements such as wires nails, pegs or screws which are to be anchored within bone. The guide body includes a top surface, a bottom surface, and a number of openings connecting the top surface with the bottom surface. The central axes of at least two of the openings are transverse to each other. The guide body permits the insertion of fixation elements at various angles with respect to each other. The guide body may prevent fixation elements which extend into the intramedullary region or the spongiosa from being displaced either in the proximal or in the distal direction.

15 Claims, 3 Drawing Sheets

(56) References Cited

U.S. PATENT DOCUMENTS

| | | | | | |
|---|---|---|---|---|---|
| 5,665,089 | A | * | 9/1997 | Dall et al. | 606/71 |
| 5,676,667 | A | * | 10/1997 | Hausman | 606/69 |
| 5,868,749 | A | * | 2/1999 | Reed | 606/76 |
| 5,893,850 | A | * | 4/1999 | Cachia | 606/72 |
| 5,904,683 | A | * | 5/1999 | Pohndorf et al. | 606/61 |
| 5,954,722 | A | * | 9/1999 | Bono | 606/61 |
| 5,976,141 | A | * | 11/1999 | Haag et al. | 606/292 |
| 6,129,728 | A | * | 10/2000 | Schumacher et al. | 606/71 |
| 6,139,552 | A | * | 10/2000 | Horiuchi | 606/88 |
| 6,306,170 | B2 | * | 10/2001 | Ray | 623/17.11 |
| 6,533,790 | B1 | * | 3/2003 | Liu | 606/73 |

FOREIGN PATENT DOCUMENTS

| | | |
|---|---|---|
| EP | 0 723 764 | 7/1996 |
| EP | 0 908 836 A2 | 4/1999 |
| FR | 742 618 | 3/1933 |
| FR | 2 254 298 | 7/1975 |
| WO | WO 96/25892 | 8/1996 |

* cited by examiner

SURGICAL GUIDE BODY

FIELD OF THE INVENTION

The invention relates to a guide body designed to receive longitudinal fixation elements and to fixation devices including such a guide body.

BACKGROUND OF THE INVENTION

A guide body may have the function of an internal fixator for osteosynthesis and may be used in the proximal part of the humerus or in other regions of long bones situated close to a joint.

A fan-like, corrugated guiding device designed to guide Kirschner wires is known from U.S. Pat. No. 5,476,467 BENOIST. This arrangement suffers from the disadvantages that the fixation elements (Kirschner wires) can only be passed through the guide parallel to each other. In addition, there is no possibility of using sutures to attach the pieces or parts of fractured bone which cannot be reached by Kirschner wires. Due to its corrugated structure, the guiding device does not rest directly on the bone, which superfluously makes it necessary to use wires of greater length.

The invention relates to a guide body designed to receive longitudinal fixation elements to be anchored within bone which makes it possible to insert fixation elements at various intersecting angles. The guide body primarily prevents the wires extending into the intramedullary region or the spongiosa from being displaced either in the proximal or in the distal direction.

Advantageously, the invention permits the use of a minimally invasive surgical technique so that the implant material to be inserted is reduced to a minimum. Due to the possibility of arranging the fixation elements in three dimensions, the guide body according to the invention is particularly suitable for osteosynthesis in cases of osteoporotic bone or bone effected by a disease. The stability of the osteosynthesis device is primarily achieved by the pegs or wires and their crosswise positioning within the bone. Due to the direct contact of the guide body with the bone, the parts of the wires to be inserted which are not in contact with the bone are reduced to a minimum. This makes it possible for the patient to put weight on the fracture site earlier, to use the injured limbs earlier and, ideally, to benefit from an accelerated healing process.

SUMMARY OF THE INVENTION

According to a preferred exemplary embodiment of the invention, one of the openings of the guide body is provided with an internal screw thread so that fixation elements having an external screw thread may also be inserted.

The openings of the guide body suitably have a diameter of between 2 and 6 mm.

According to a preferred exemplary embodiment of the invention, the guide body is provided with a number of additional holes arranged in the edge portion of the guide body, so that it is possible, if necessary, to fix parts of fractured bone to the plate by means of sutures. The term 'edge portion' is to be understood here as referring to a zone not exceeding 10 mm in width. These additional holes should suitably not have any sharp edges so as to prevent the sutures fixed therein from being damaged. Suitably, the number of such additional holes is between 4 and 6, the hole diameter being between 1.5 and 2.5 mm.

According to a further preferred exemplary embodiment of the invention, the guide body consists of a plurality of grids, preferably made of metal wire, which are stacked on one another and maintained in their relative position by a frame, the superimposed meshes of the grids forming the openings. The Kirschner wires may be driven through the grid meshes at angles and in positions which are freely selectable and they are maintained in their relative positions by means of the wire grids stacked on one another.

Preferably, the Kirschner wires are provided with a screw thread designed to engage with the wire grid so as to prevent the wires from getting out of place. This exemplary embodiment of the invention presents the advantage that the positions and the angles of the Kirschner wires are not predefined but may be freely selected according to the particularities of the fracture to be treated.

Preferably, 2 to 8 (typically 4 to 6) of such grids are stacked right on one another in order to achieve a minimal overall height of the implant. The mesh size of the grids preferably ranges between 1.5 and 2.0 mm and should generally be smaller than the diameter of the Kirschner wires which are used as fixation elements. The individual grids should be stacked in such a way that no two grids will have the same position (structure) relative to each other. The angle of rotation between the individual grid layers to provide an offset therebetween will accordingly be defined by the number of grids used (e.g. 60 degrees with 6 grids). The wires forming the individual grids preferably have a thickness of between 0.2 and 0.6 mm.

The Kirschner wires used as fixation means are preferably provided with an external screw thread. At least part of the openings of the guide body should be provided with an internal screw thread corresponding to the external screw thread of the Kirschner wires. Preferably, the fixation element is provided with a headless rear end portion and has a uniform diameter over its entire length. On its front end portion, which may correspond to between ten and fifty percent of the total length, the fixation element is preferably provided with a non-threaded portion. The fixation element has a diameter ranging between 2 and 6 mm and the mesh size of the grids should be inferior to the diameter of the fixation element.

According to a preferred exemplary embodiment of the invention, the fixation device including the guide body additionally comprises at least one hollow, cylindrical connecting piece provided with a concentrical bore which is insertable into the openings of the guide body in such a way as to be in frictional or positive engagement therewith. The fixation element may be kept in place within the hollow, cylindrical connecting piece by means of press fit, force fit or friction.

BRIEF DESCRIPTION OF THE DRAWINGS

In the following, the invention and exemplary embodiments of the invention will be illustrated in greater detail with reference to the partially diagrammatic representations of several embodiments.

DETAILED DESCRIPTION OF THE INVENTION

Figure 1:
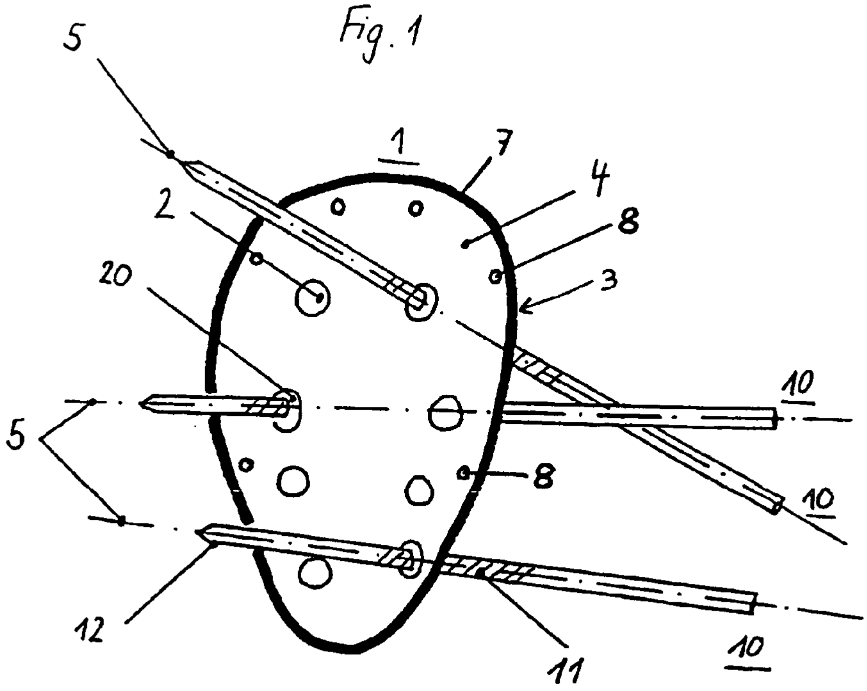
FIG. 1 shows a perspective view of an exemplary embodiment of a guide body with Kirschner wires inserted therein according to the present invention.

The guide body shown in FIG. 1 consists of a flat or curved plate having a thickness of between 2 and 5 mm, made of metal materials suitable for implants or of plastic materials (including biodegradable plastic materials). The plate has a plurality of openings 2 in the form of bores which have a diameter of between 2 and 6 mm and which connect the top surface 3 with the bottom surface 4 of the guide body 1. The openings 2 are arranged in such a way that the centers of at least three of them are not situated on a straight line. The openings 2 serve for receiving surgical fixation elements 10 such as wires, nails, pegs or screws having a diameter of between 2 and 6 mm. In FIG. 1 these elements are Kirschner wires with an external screw thread 11 and a sharp front end 12. The central axes 5 of at least two of these openings 2 are skewed in relation to each other, so that the fixation means 10 may be three-dimensionally arranged. The central axes 5 of the openings 2 preferably form an angle of between 50 and 90 degrees relative to the plane of the plate-like guide body 1.

On the edge portion 7 of the guide body 1 six additional holes 8 are provided which have a diameter of 2 mm and serve for the fixation of sutures, as described below.

The bottom surface 4 of the guide body 1 is preferably adapted to the form of the bone surface to which it is to be applied in order to form a sufficiently large contact surface with the bone.

Figure 2:
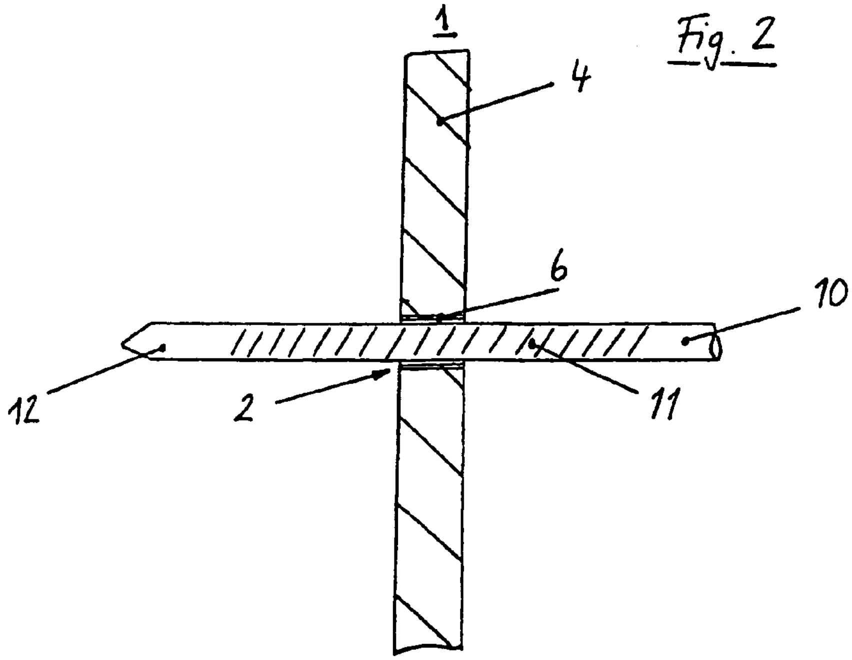
FIG. 2 shows a cross-sectional view of the guide body of FIG. 1 taken proximate the region of a Kirschner wire inserted therein.

As shown in FIG. 2, the openings 2 shaped in the form of bores may be provided with internal screw threading 6 which corresponds to the external screw threading 11 of the fixation means 10. Preferably, the fixation element 10 is provided with a headless rear end portion and thus has a uniform diameter over its entire length, which makes it possible to use conventionally shaped Kirschner wires. Furthermore, on its front end portion 12, which may correspond to between ten and fifty percent of the total length of the fixation element 10, said fixation element 10 is provided with a non-threaded portion. The screw thread is only necessary for the fastening of the fixation element 10 in the plate-like guide body 1, and not for its fixation in the bone.

Figure 3:
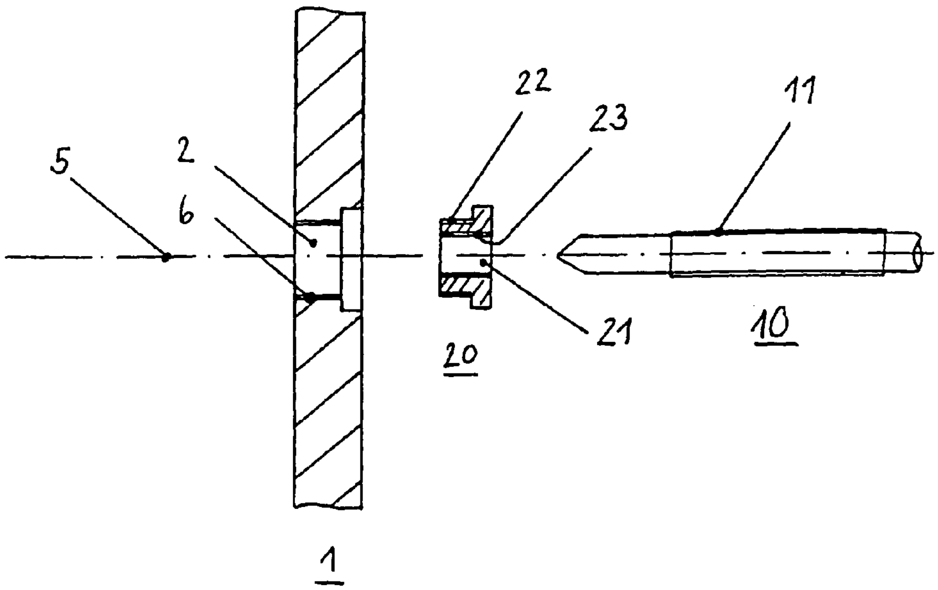
FIG. 3 shows a cross-sectional view of the guide body taken proximate the region of an opening therein and including a threaded connecting piece insertable into said opening and a fixation means insertable into said connecting piece.

FIG. 3 shows a preferred embodiment of a fixation device including a guide body 1 in which a hollow, cylindrical (or a hollow, conical) connecting piece 20 with a concentrical bore 21 is included which is insertable into the opening 2 in such a way as to be in frictional or positive engagement therewith. The connecting piece 20 may be inserted in a simple manner into the opening 2 where it will be retained by the force of friction, provided that it exactly fits the opening. It may, however, also be equipped with external screw threading 22 which matches the internal screw threading 6 of the opening 2.

In this case, the fixation means 10, instead of being passed directly through the opening 2, may be passed through the concentrical bore 21 of the hollow, cylindrical connecting piece 20. Inside the connecting piece 20, an internal screw threading 23 is provided which corresponds to the external screw threading 11 of the fixation means 10. The fixation means 10 may also be non-threaded and may be fastened within the guide body 1 merely by means of a radial clamping exerted by the connecting piece 20.

Figure 4:
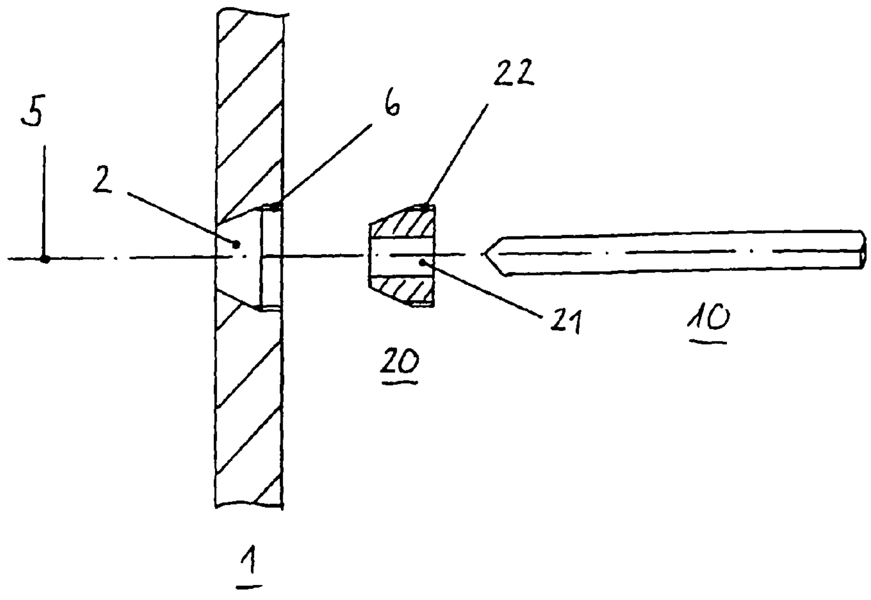
FIG. 4 shows a cross-sectional view of the guide body taken proximate the region of an opening therein and including a non-threaded connecting piece insertable into said opening and a fixation means insertable into said connecting piece.

In another embodiment, shown in FIG. 4, the connecting piece 20 is in the form of a conical collet chuck or vice chuck which is insertable into a corresponding, conically shaped opening 2 of the guide body 1 in such a way as to be frictionally engaged, so that no screw threads are necessary.

The guide body 1 may be introduced into the patient's body through a minimal incision made for example in the region of the proximal humerus to which said guide body may be fastened by means of the fixation means 10. The additional use of bone cement as a reinforcement is not precluded. As the plate has a sufficient number of openings 2 as well as additional holes 8 located in the edge portion 7 of the guide body 1 the latter of which are specifically designed for fixing sutures thereto, these may serve for fastening bands to bone fragments of the humerus. The three-dimensional arrangement of the fixation means 10 prevents them from becoming loose, which results in a substantially improved overall stability of the fixation device.

Figure 5:
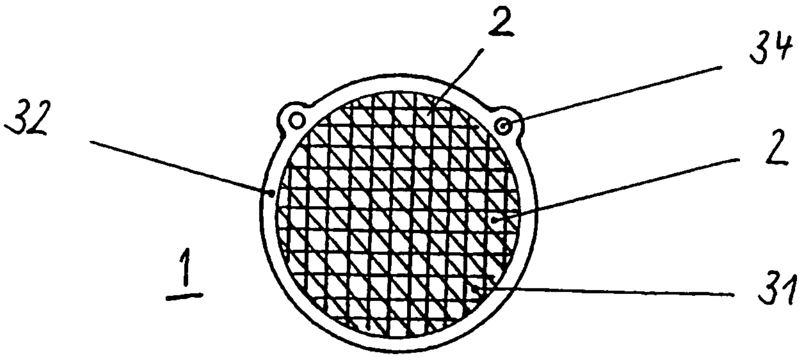
FIG. 5 shows a perspective view of a guide body consisting of a multilayer wire grid.

In a further embodiment of the guide body 1, shown in FIG. 5 (in the form of a guide plate), the fixation elements 10 are kept in place and stabilized in their respective angular positions by means of a multilayer mesh grid 31 held together by the frame 32. The fixation elements 10 are driven directly through the multilayer grid 31. This may be done in any position all over the diameter defined by the individual openings 2. The lateral holes 34 arranged on the frame 32 may serve for fastening the guide body 1 by means of sutures.

Figure 6:
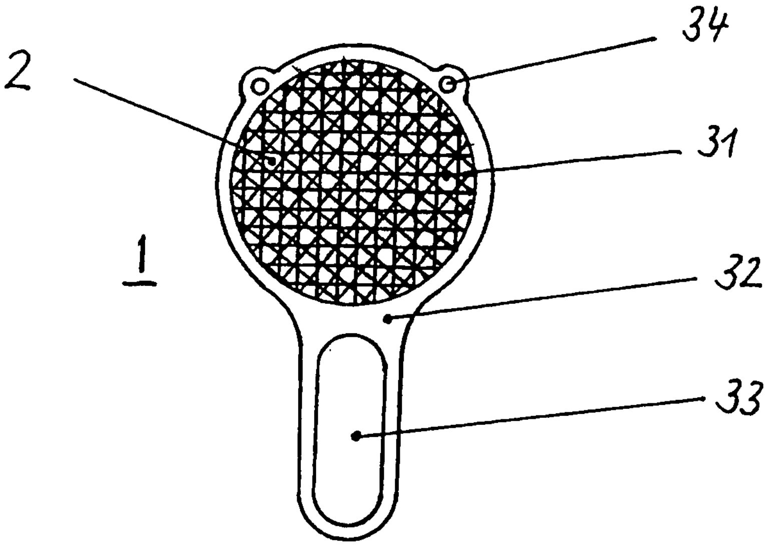
FIG. 6 shows a perspective view of a guide body consisting of a multilayer wire grid and a lip for receiving a fastening screw.

In a variant of the guide body 1 of FIG. 5, as shown in FIG. 6, guide body 1 additionally comprises an elongate hole 33 in the form of a lip arranged on the frame 32 which might also be in the form of a normal, circularly cylindrical hole. It serves for receiving a screw (not shown in the drawing) by means of which the guide body 1 may be fastened to the bone before the fixation elements 10 are driven through the guide body 1 and extend into the bone.

In the embodiments according to FIGS. 5 and 6, the fixation elements 10 to be used (typically in the form of Kirschner wires) have an external screw thread in order to prevent them from being displaced.

What is claimed is:

1. A guide body for receiving fixation elements to be anchored in bone, the guide body comprising:

a plate having a top surface, a bottom surface for contacting bone, and a number of openings between the top and bottom surfaces; and at least one connecting piece for insertion into one of the openings, the at least one connecting piece having a bore therein for receiving a surgical fixation element, and comprising internal threading and external threading, wherein each connecting piece is configured and dimensioned to be received in one of the openings and retained therein by frictional or positive engagement, and the combination of plate openings and connecting pieces provides transverse paths for guiding surgical fixation elements into bone;

wherein the plate further comprises an edge portion and a number of holes disposed in the edge portion, an axis of each of the holes intersecting the top and bottom surfaces; and wherein the holes have smaller diameters than the openings.

2. The guide body of claim 1, wherein at least one of the openings comprises internal threading.

3. The guide body of claim 1, wherein the openings have a diameter between 2 mm and 6 mm.

4. The guide body of claim 1, wherein the number of holes is at least four and no more than six.

5. A guide body of claim 1, wherein the holes have diameters between 1.5 mm and 2.5 mm.

6. A guide body of claim 1, wherein the surgical fixation element is selected from the group consisting of a wire, nail, peg and screw.

7. The guide body of claim 1, wherein at least two openings each have a central axis, and wherein the central axes are askew.

8. The guide body of claim 1, wherein the plate is comprised of metal.

9. The guide body of claim 1, wherein the plate is comprised of plastic.

10. The guide body of claim 9, wherein the plastic is biodegradable.

11. The guide body of claim 1, wherein the plate has a thickness between about 2 mm and about 5 mm.

12. The guide body of claim 1, wherein the plate is substantially flat.

13. The guide body of claim 1, wherein the plate is substantially curved.

14. The guide body of claim 1, wherein at least one connecting piece is substantially cylindrical.

15. The guide body of claim 1, wherein at least one connecting piece is substantially conical.

* * * * *